(12) United States Patent
Gillies

(10) Patent No.: US 8,258,368 B2
(45) Date of Patent: Sep. 4, 2012

(54) REUSABLE DIAPER COMPOSITIONS

(76) Inventor: Suzanne Gillies, King City (CA)

( * ) Notice: Subject to any disclaimer, the term of this patent is extended or adjusted under 35 U.S.C. 154(b) by 351 days.

(21) Appl. No.: 12/718,029

(22) Filed: Mar. 5, 2010

(65) Prior Publication Data

US 2010/0228216 A1 Sep. 9, 2010

(30) Foreign Application Priority Data

Mar. 5, 2009 (CA) ...................................... 2657077

(51) Int. Cl.
*A61F 13/15* (2006.01)
*B32B 37/00* (2006.01)

(52) U.S. Cl. ................. 604/378; 604/385.101; 604/367; 604/374; 604/375; 604/377; 156/164

(58) Field of Classification Search .................. 604/378, 604/385.101, 367, 374, 375, 377; 156/164
See application file for complete search history.

(56) References Cited

U.S. PATENT DOCUMENTS 5,267,991 A 12/1993 Gillies et al.

*Primary Examiner* — Jacqueline F. Stephens
(74) *Attorney, Agent, or Firm* — McMillan LLP

(57) ABSTRACT

A reusable and absorptive mat for the absorption, dispersion and retention of a liquid is disclosed. The absorptive mat comprises a plurality of non-woven layers, of carded and randomly laid viscose rayon fibres having a cross-section of substantially rigid multi-limbed configuration. The layers are stitchbonded in an as laid state, thereby substantially limiting entanglement and breaking of individual fibres. The stitchbonding is performed with a thread under limited tension so as to maintain uniformity of the absorptive mat. Also disclosed is a method of manufacturing a reusable and washable article for the absorption, dispersion and retention of a liquid comprising providing a plurality of viscose rayon fibres, carding the plurality of fibres, randomly laying the carded fibres into a continuous random web structure and stitchbonding the continuous random web structure in an as laid state.

21 Claims, 5 Drawing Sheets

REUSABLE DIAPER COMPOSITIONS

FIELD OF THE INVENTION

The present invention relates to reusable diaper compositions and more specifically to a reusable and absorptive mat for the absorption, dispersion and retention of a liquid manufactured so as to minimize interference with the inherent absorbent properties of viscose rayon fibres.

BACKGROUND OF THE INVENTION

The majority of diapers in use today, both for adults and children are of the disposable type. Over time, disposable diapers have presented improved comfort levels, fluid absorption and dispersion and typically include a layer in contact with the skin that feels dry over extended periods of time. These advances in disposable diapers, at one point rendered conventional cotton or flannel diapers almost obsolete.

A major drawback of disposable diapers is that they are not readily biodegradable and with ever increasing use, this has resulted in an overload at garbage and landfill sites to the point of causing serious environmental problems. Furthermore, disposable diapers or incontinence pads from hospitals are treated as infectious waste and must be disposed of at special landfill sites, thereby adding to the critical storage at such sites.

With the recent increase in public awareness and concern with environmental issues along with a move towards reducing waste, there has been renewed interest in washable and reusable diapers. This interest is however constrained by the performance of reusable and washable diapers when compared with the advances in disposable diapers. To date, disposable diapers and incontinence pads are used in the overwhelming majority of cases as their comfort, dryness and absorption qualities have been superior to those of reusable diapers and incontinence pads. Due to the competitive marketplace and high demands and expectations of users, there is a need in the art for an improved reusable and washable diaper which provides equivalent comfort, dryness and absorption qualities as disposable diapers.

One prior art reusable diaper, disclosed in U.S. Pat. No. 5,267,991 (Dec. 7, 1993) to Gillies et al. (hereinafter, the '991 Patent), attempted to match the performance of disposable diapers with the inclusion of an absorbent mat produced using a viscose rayon fibre developed by Cortaulds Limited and produced under the GALAXY™ and GALAXY I™ brands. The GALAXY I™ fibre, having a trilobal configuration, was found to have a relatively even fluid dispersion characteristic making it ideal for use in reusable diapers. Both the aforementioned fibres exhibited a water imbibition characteristic of from 100-345%.

While the use of viscose rayon fibres in applications requiring high absorption, such as tampons, was known, the '991 Patent disclosed a method for forming the viscose rayon fibres into a washable and reusable mat, thus allowing them to be used in reusable diaper or incontinence pad applications. The method included providing a plurality of non-woven layers of carded and cross-laid viscose rayon fibres having a cross-section of substantially rigid, multi-limbed configuration and stitchbonding said layers into a cohesive web with a thread under medium tension to stabilize and maintain the web such that the fibres that are gripped by the threads are not bunched up and tightened in a manner that would interfere with uniform absorption and dispersion of a fluid being absorbed.

The carding and cross-laying steps are well known in the art of producing fabrics. Cross-laying involves laying the fibres in layers offset by ninety degrees until a desired thickness is reached. With the viscose rayon fibres, this allows for fluid dispersion optimized along each fibre and therefore fluid is drawn substantially along the two axes as they are cross-laid. This dispersion, while far superior to traditional cotton diapers, needs to be improved upon to match the absorption and dispersion characteristics of current disposable diapers. There is thus a need in the art for a reusable and washable diaper which provides improved fluid absorption and dispersion.

The stitchbonding step of the '991 Patent was carried out using a MALLYMO® stitchbonding machine made by Textina Inc. As is well known and common practice in the art, prior to stitchbonding, the fabric or web to be stitchbonded is temporarily bonded or otherwise held cohesively such that the web can be maintained in a given shape and fed easily through the stitchbonding machine. This results in a stitchbonded mat having a substantially controlled shape. Typically, as in the manufacture of felt, such pre-stitchbonding processing steps involve a chemical or thermal bonding; however these preliminary steps were found by the inventor to interfere with the absorbency of the viscose rayon fibres, and were for this reason unsuitable for use in the method of the '991 Patent. The alternative, as carried out when using a MALLYMO® stitchbonding machine is to use a needle punch machine, (which, contrary to the suggestion of its name, uses no thread) prior to feeding the web therethrough for stitchbonding. A needle punch machine causes some fibres to break or to entangle with others, thereby constraining the web for easier feeding through the stitchbonding machine.

It has also been found by the inventor that the needle punch step, while not limiting absorbency to the same degree as chemical or thermal bonding, still results in less than optimal absorbency and fluid dispersion due to breakage and entanglement of the fibres that make up the web. This is so, as it has been found that fluid dispersion is optimized along the length of a given individual fibre. Accordingly, broken web fibres result in the stitchbonded threads not gripping entire fibres, with a resultant loss of directionality of individual fibres within the web. Similarly, entangled fibres lose the original directionality with which they were laid within the web. Both effects combine to cause reduced fluid dispersion through the web away from a potential source of wetting. Thus, using a needle punch to pre-process a fibrous web prior to stitchbonding has the effect of reducing the overall moisture absorption capacity of the web. Such reduced moisture retention capacity has been a barrier to more widespread use of reusable diapers, as they continue to underperform in comparison to disposables.

Another problem associated with prior art reusable diapers is the loss of integrity after repeated washings. This can be caused by shrinking, change of shape, or degradation in the quality of the absorbent mat.

There is therefore a need in the art for a reusable and washable diaper or mat composition which provides improved fluid absorbency and fluid dispersion characteristics over the prior art and comparable to those of disposable diapers. Moreover, there is a further need for a reusable and washable diaper which can maintain its size, shape and form after repeated washings.

SUMMARY OF THE INVENTION

In accordance with a first embodiment of the present invention there is disclosed a reusable and absorptive mat for the absorption, dispersion and retention of a liquid comprising a plurality of non-woven layers, of carded and randomly laid viscose rayon fibres having a cross-section of substantially rigid multi-limbed configuration, said layers stitchbonded in an as laid state, thereby substantially limiting entanglement and breaking of individual fibres, with a thread under limited tension so as to maintain uniformity of the absorptive mat.

In accordance with one aspect of the first embodiment, the viscose rayon fibres are of a trilobal configuration and have a water imbibition characteristic of from 100 to 345 percent.

In accordance with a further aspect of the first embodiment, the layers are stitchbonded with a polyester thread in rows approximately 2 to 10 rows per inch, each of said rows having from 6 to 200 stitches per inch.

In accordance with a further aspect of the first embodiment, said absorptive mat is pre-shrunk.

In accordance with a second embodiment of the present invention, there is disclosed a reusable diaper comprising, a layer of a hydrophobic web of polyester fibres, an impermeable pant-like garment and a reusable and absorptive mat as herein disclosed, said absorptive mat disposed within said garment and said hydrophobic web adjacent to said absorptive mat.

In accordance with a third embodiment of the present invention, there is disclosed a washable and reusable incontinence pad for the absorption, dispersion and retention of liquids, said pad comprising an interior layer of hydrophobic material including a receiving surface, at least one median layer adjacent the interior layer opposite the receiving surface and comprising a plurality of non-woven layers, of carded and randomly laid viscose rayon fibres having a cross-section of substantially rigid multi-limbed configuration, said layers stitchbonded in an as laid state, thereby substantially limiting entanglement and breaking of individual fibres, with a thread under limited tension so as to maintain uniformity of the absorptive mat, and an outer layer of substantially waterproof polyurethane film adjacent the median layer.

In accordance with one aspect of the third embodiment, said interior layer, said at least one median layer, and said outer layer are joined only along outer edges thereof.

In accordance with a further aspect of the third embodiment, said interior layer and said outer layer are joined to form an interior pocket for holding said at least one median layer.

In accordance with a further aspect of the third embodiment, said at least one median layer comprises two median layers.

In accordance with a further aspect of the third embodiment, said viscose rayon fibres include recycled viscose rayon fibres.

In accordance with a further aspect of the third embodiment, said viscose rayon fibres are blended with between 5% and 40% polyester fibres.

In accordance with a further aspect of the third embodiment, said viscose rayon fibres are of trilobal configuration and have a water imbibition characteristic of from 100 to 345%.

In accordance with a further aspect of the third embodiment, said layers of viscose rayon fibres are stitchbonded with polyester thread along a series of rows spaced approximately 2 to 10 rows per inch with each of said rows having from 6 to 200 stitches per inch.

In accordance with a further aspect of the third embodiment, said interior layer is characterized by being warp knit tricot stitched, and said receiving surface is napped finish.

In accordance with a further aspect of the third embodiment, wherein said outer layer comprises a first lamina of pre-stretched film of polyurethane bonded to a second lamina comprising a web of warp knit tricot stitched polyester fibres and in which said first lamina is positioned adjacent said median layer.

In accordance with a further aspect of the third embodiment, said median layer is preshrunk.

In accordance with a further aspect of the third embodiment, said pad is contoured in an hourglass shape for wearing as a diaper and has a fastener device for securing said pad about a wearer.

In accordance with a further aspect of the third embodiment, the median layer as hereinbefore disclosed in combination with a mesh liner for receiving and disposing of solid excrement, said mesh liner placed adjacent said receiving surface of said interior layer.

In accordance with a fourth embodiment of the present invention, there is disclosed a method for manufacturing a reusable and washable article for the absorption, dispersion and retention of a liquid comprising providing a plurality of viscose rayon fibres having a cross-section of substantially rigid multi-limbed configuration, carding said plurality of viscose rayon fibres, randomly laying the carded plurality of viscose rayon fibres into a continuous random web structure to form a desired thickness, and stitchbonding said continuous random web structure in an as laid state thereby limiting entanglement or breakage of individual fibres to form an absorptive mat.

In accordance with one aspect of the fourth embodiment, said viscose rayon fibres are of a trilobal configuration and have a water imbibition characteristic of from 100 to 345 percent.

In accordance with a further aspect of the fourth embodiment, said stitchbonding step comprises stitchbonding with polyester thread in rows approximately 2 to 10 rows per inch, each of said rows having from 6 to 200 stitches per inch.

In accordance with a further aspect of the fourth embodiment, subjecting the stitchbonded mat to a heat treatment to reduce shrinkage when washed after use.

In accordance with a further aspect of the fourth embodiment, said heat treatment is at approximately 110° C.

In accordance with a further aspect of the fourth embodiment, providing an interior layer of hydrophobic material having a receiving surface, said interior layer adjacent said absorptive mat opposite the receiving surface and providing an outer layer of substantially waterproof polyurethane film adjacent said absorptive mat.

In accordance with a further aspect of the fourth embodiment, adjoining said interior layer, said absorptive mat and said outer layer along the outer edges thereof to form a pad of unitary construction.

In accordance with a further aspect of the fourth embodiment, adjoining said interior layer and said outer layer to form an envelope, said absorptive mat located within said envelope.

In accordance with a further aspect of the fourth embodiment, said article is contoured in an hourglass shape for wearing as a diaper and further providing a fastener for securing said diaper about a wearer.

It is thus an object of this invention to obviate or mitigate at least one of the above mentioned disadvantages of the prior art.

Other advantages, features and characteristics of the present invention, as well as methods of assembly, use, operation and functions of the related elements of the structure, and the combination of parts and economies of manufacture, will become more apparent upon consideration of the following detailed description and the appended claims with reference to the accompanying drawings, the latter of which is briefly described hereinbelow.

BRIEF DESCRIPTION OF THE DRAWINGS

FIG. 5b of the drawings is a bottom perspective view of the diaper of FIG. 5a.

DETAILED DESCRIPTION OF PREFERRED EMBODIMENTS OF THE INVENTION

A reusable and washable absorptive mat 10 constructed according to the present invention has been found to have improved absorption and dispersion characteristics over the prior art by virtue of improvements to the structure of the absorptive mat and the method of manufacture as detailed below. The reusable and washable absorptive mat 10, while described for use in a diaper 200, or in an incontinence pad 100, is not limited as such, and can be used in any application requiring a reusable and absorptive mat for the absorption, dispersion and retention of a fluid.

Figure 4:
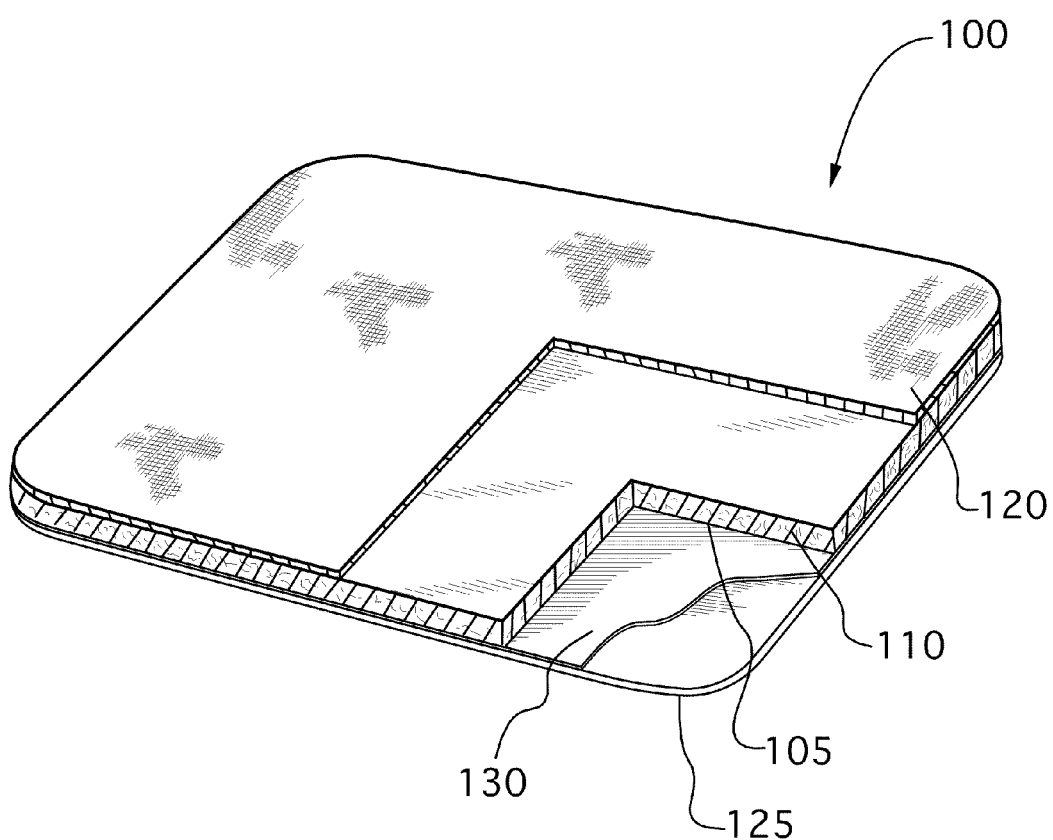
FIG. 4 of the drawings is a top perspective view of an incontinence pad according to a third embodiment of the present invention.
Figure 5A:
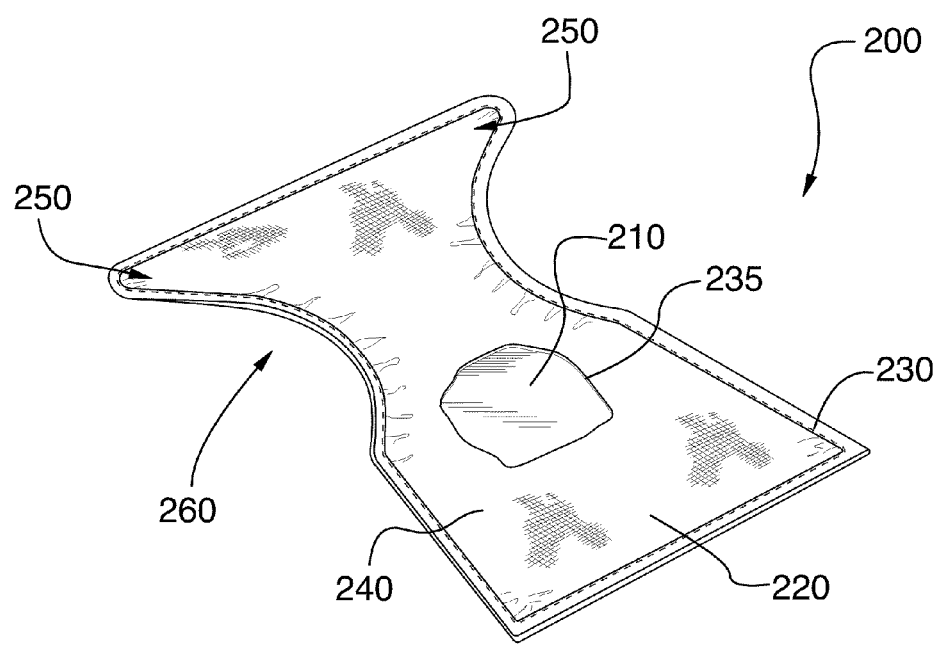
FIG. 5a of the drawings is a top perspective view of a diaper according to a second embodiment of present invention.
Figure 5B:
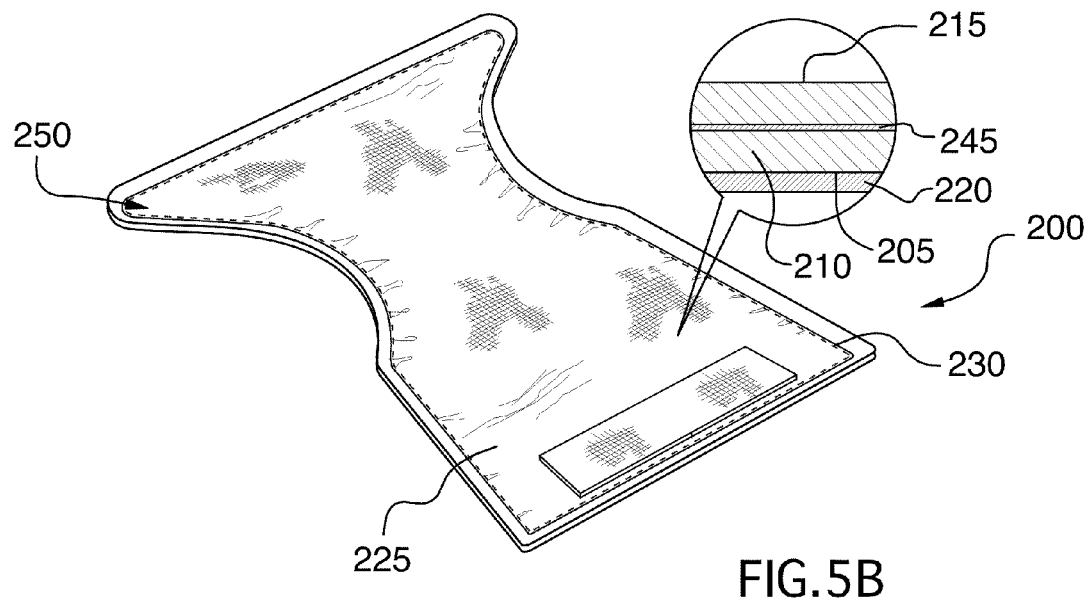

As shown in either FIG. 4, an incontinence pad 100, or in FIGS. 5A and 5B, a reusable diaper 200 constructed according to the present invention comprises three layers: an inner layer of hydrophobic material 120 or 220 for contacting the skin on an interior surface, a median layer 110 or 210 comprising the aforementioned absorptive mat 10 (as shown separately in FIG. 2) and being positioned opposite to the interior surface of the inner layer 120 or 220 for providing the required fluid absorption, retention and dispersion characteristics, and an outer layer 125 or 225 of substantially waterproof material enclosing the median layer 110 or 210 within the inner layer 120 or 220 and the outer layer 125 or 225. It is the median layer 110 or 210 and improvements thereto which comprise the characteristics of the present invention. As previously noted, other applications for an absorptive mat 10 herein used as the median layer 110,210 in a diaper 200 or incontinence pad 100 are within the scope of the present invention.

Figure 6:
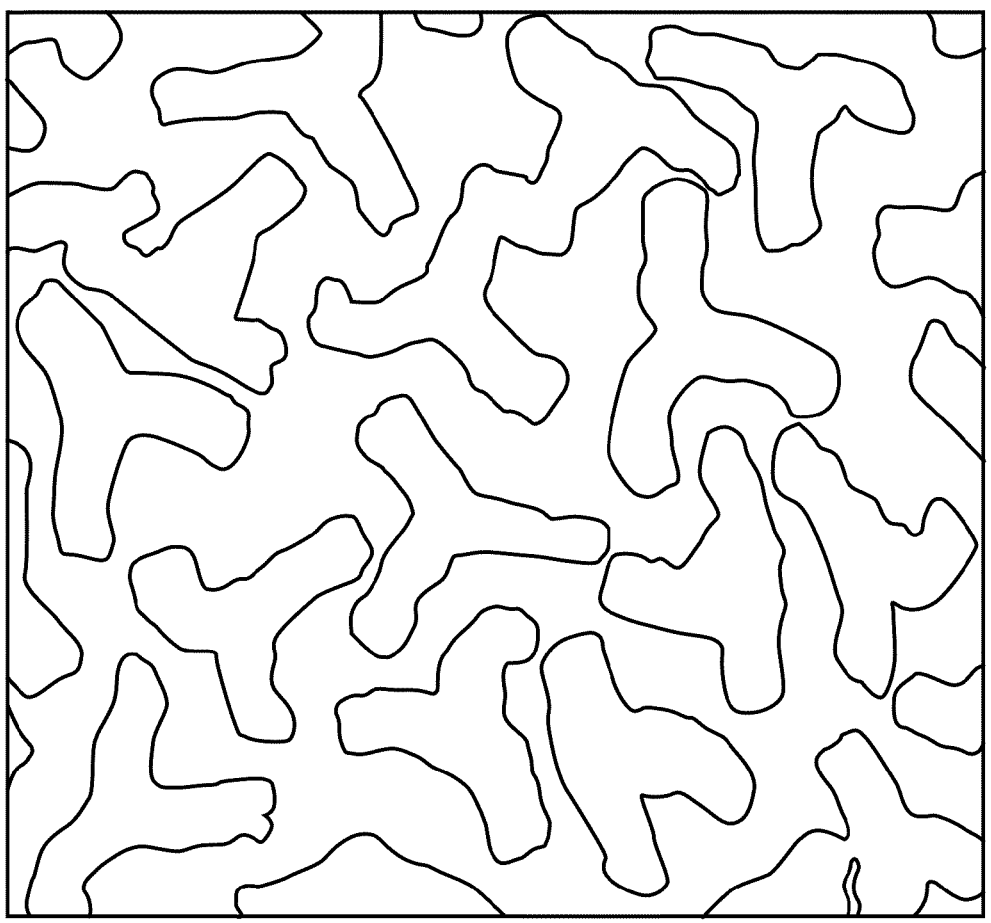
FIG. 6 of the drawings is a cross-sectional schematic depiction of trilobal fibres as used in the present invention.

A reusable and washable absorptive mat 10 for the absorption, retention and dispersion of a fluid according to the present invention is produced from viscose rayon fibres 15 having a cross-section of substantially rigid multi-limbed configuration, for example those produced by Courtaulds Limited of London, England under the GALAXY I™ brand. In their pre-processed state, multi-limbed viscose rayon fibres, either trilobal or multilobal were found to have a water imbibition characteristic of 100 to 345 percent, measured by dividing a wet weight by a dry weight of a given sample of the fibre. The fibres are to be formed into a non-woven mat. FIG. 6 is a schematic depiction of the trilobal fibres preferably used in the present invention.

Figure 3:
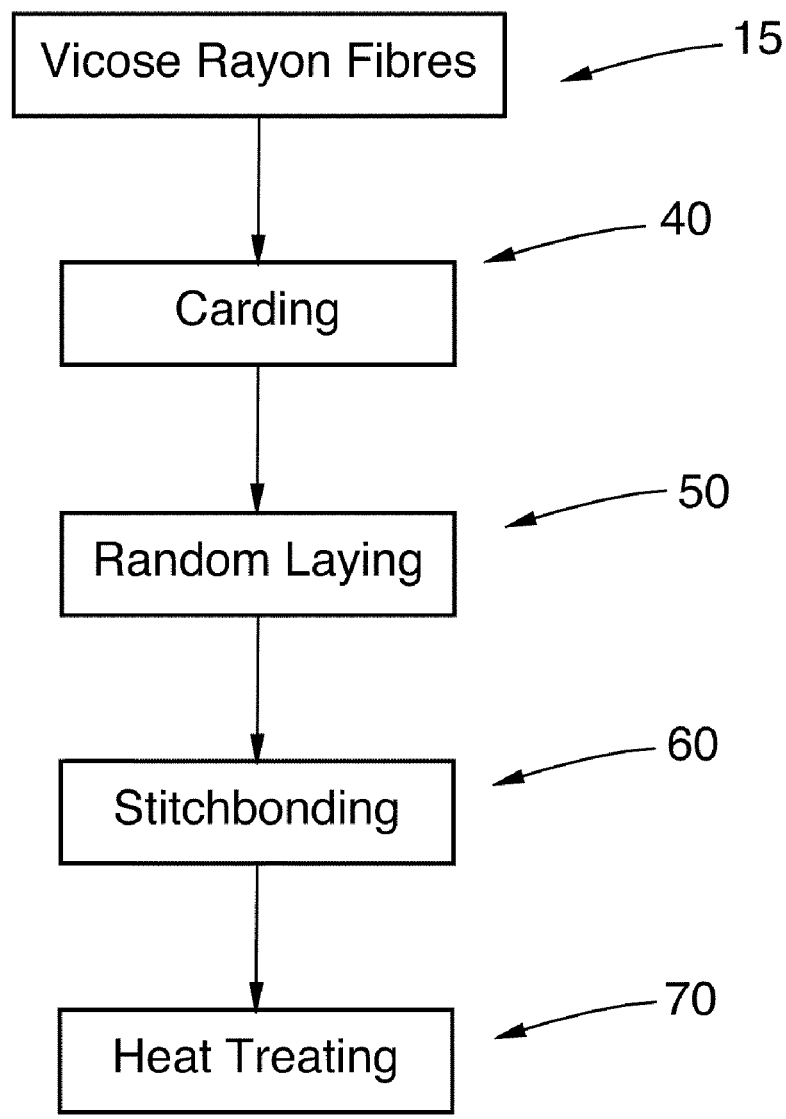
FIG. 3 of the drawings is a flowchart showing the method of manufacturing a reusable and absorptive mat according to a fourth embodiment of the present invention.

The viscose rayon fibres 15 as described above are processed into the absorptive mat 10 according to the present invention as herein described. Referring now to FIG. 3, and more particularly to step 40, the viscose rayon fibres 15 are first carded to orient and arrange them into a form which can be made into a web, as is well known in the art. Often times in the art, a fibre opener device, also referred to as a fine opener, is installed in parallel with a carding machine such that the fibres are opened and separated prior to carding. According to the present invention, the fibres are preferably carded without pre-processing through a fibre opener. Fibre opener devices typically result in a high breakage rate of fibres and, therefore, the fibres of the present invention are carded in their provided state.

Figure 1:
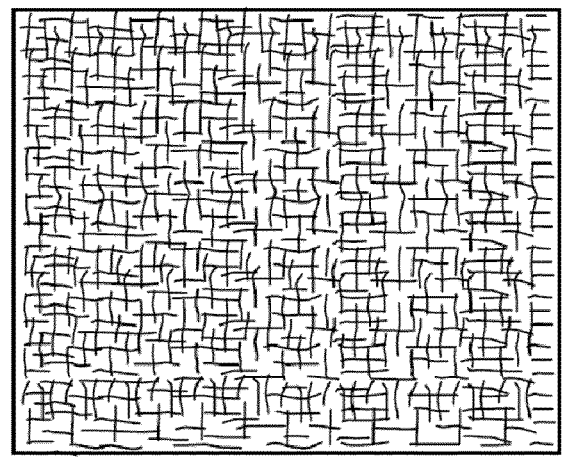
FIG. 1 of the drawings is a top plan view depicting the cross-laid fibres of an absorptive mat according to the prior art.
Figure 2:
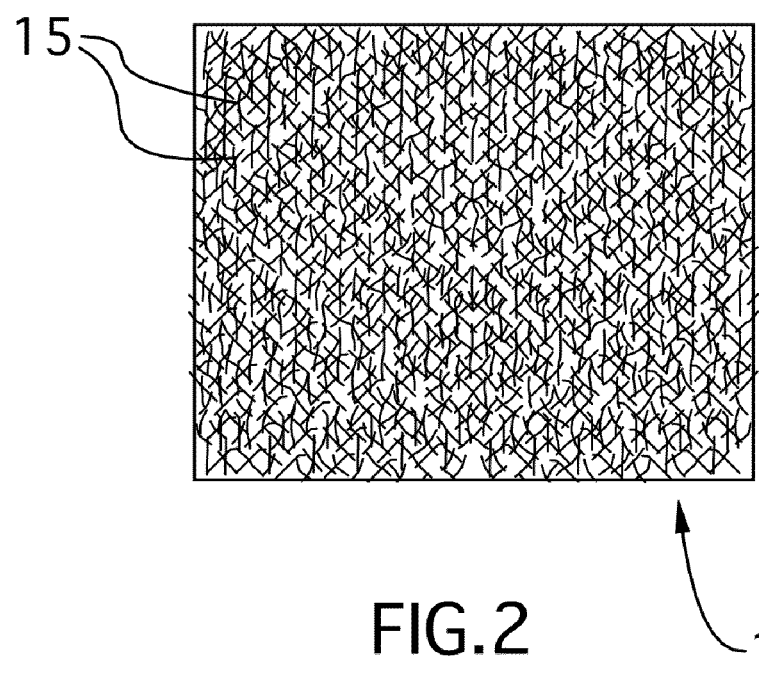
FIG. 2 of the drawings is a top plan view schematically depicting the randomly laid fibres of an absorptive mat according to a first embodiment of the present invention.

Next, referring to step 50, the carded viscose rayon fibres are randomly laid into a continuous random web structure until a desired thickness is reached. The randomly laying of the carded fibres can be done using a Rando-Webber® or as part of the Rando-Web® process developed by the Rando® Machine Corporation of Macedon, N.Y., USA. FIG. 2 schematically shows the randomly laid web structure of the present invention. For ease of illustration, only a limited number of layers are shown in FIG. 2, however, it will be understood by those skilled in the art that the directions of the fibres 15, and the number of layers in the web are not limited to those shown in FIG. 2. The random web of the present invention allows dispersion of an absorbed fluid in all directions from an original source of the fluid. Subsequent layers of carded fibres are arranged at a random angle offset from the fibres of the previous layer. The result is the fibres of each successive layer are oriented in a different direction allowing for fluid dispersion in a given layer according to its fibre orientation and fluid dispersion across the thickness of the web in an unlimited number of random directions. In contrast to the prior art teaching, which included only cross-laying and thus fluid dispersion essentially along two perpendicular axes, the random laying allows for dispersion in all radial directions away from the fluid source. This allows for faster and more even fluid dispersion. The faster and more even dispersion is a function of the viscose rayon fibres which absorb and disperse fluid along the length of each fibre.

Alternatively, the carded fibres can be laid into a radial web, wherein the fibres of each successive layer are offset at a given angle from the previous layer. The result is a web laid in a radial manner.

Referring now to step 60, the carded and randomly laid random web structure is then stitchbonded in an as laid state. For the purposes of the present invention, application, specification, and claims, an "as laid state" is defined as the state of the continuous random web structure immediately after being laid into the desired thickness, without the inclusion of any preparatory steps to aid in the stitchbonding process. More specifically, the "as laid state" is defined expressly to exclude any needling or needle punching of the web or any other process known in the art to provide for easier feeding into a stitchbonding machine at the expense of potentially altering the state of individual fibres within the web, such as by breaking or entangling them.

The prior art step of needling is carried out in the prior art to provide a more cohesive web to be transferred from the carding machine, for subsequent feeding through the stitchbonding machine. This step is well established and thought necessary in the prior art to provide for a more uniform web for feeding through the stitchbonding machine. It was found by the present invention, however, that needle punching results in significant breaking or entanglement of individual fibres, thereby hampering the fluid dispersion and absorption characteristics of the absorptive mat; accordingly, this preprocessing step is explicitly and expressly excluded from the present invention. In order to eliminate the temporary binding and shaping of the web provided by needling, greater care must be taken in transporting the web from the carding machine and subsequently feeding same into the stitchbonding machine.

If transporting the non-needled web from the carding machine to the stitchbonding machine is required, mechanical means may be used to assist therein, which means does not cause breakage or entanglement of individual fibres. One such mechanical means is the Menzel "A-Frame", manufactured by Menzel (USA) of Sparttanburg, S.C., which can be used for transferring un-needled webs. The Menzel "A-Frame" is designed to wind and unwind a wide variety of fabrics or webs on and off of fixed mounted cores. The versatility of the Menzel "A-Frame" does not require the web to be bonded or held cohesively to be transported to, or fed into, a stitchbonding machine without damage. Optionally, the web may be surrounded by a polyethylene, or similar material, film to maintain cohesiveness in transporting onto and off from the Menzel "A-Frame". Other means which do not cause or limit the breakage or entanglement of individual fibres, including but not limited to, mechanical clamping means, other mechanisms for winding onto and from a core, and manual feeding of the web, are all within the scope of the present invention.

Preferably, the stitchbonding step 60 is thereafter carried out using a polyester thread having a thickness of approximately 150 denier. Some variation in the thickness of the thread, or an optimal thickness for a given mat size, as determined by routine experimentation, is contemplated by the present invention. The stitchbonding is preferably carried out using multiple needles to provide a series of stitch rows spaced apart to give approximately 2 to 10 rows per inch, with approximately 5 rows per inch, being the most preferable for diaper purposes. Each row contains approximately 60 to 200 stitches per inch, with 120 stitches per inch being the most preferred.

The non-woven web is stitchbonded under limited, or relatively light, tension so that the fibres gripped by the thread are not bunched up and tightened in a manner that would interfere with the uniformity of the absorptive mat 10. Maintaining a high degree of uniformity in the absorptive mat 10 ensures minimal interference with uniform absorption and dispersion. As can be appreciated, bunching at the stitchbonded areas results in regions of higher concentration of fibres and disrupts the even and uniform absorption and dispersion of fluids. The limits on the thread tension are dependent on the thickness of web, or intended thickness of the final absorptive mat 10, for a given application, and can optionally be determined by visually observing the web for regions of bunching or fluffiness.

After stitchbonding, the absorptive mat is pre-shrunk by subjecting it to an air heat treatment, preferably at approximately 110° Celsius. This allows the diaper to maintain a consistent size, shape and form after repeated washings.

To further increase the strength of the absorptive mat 10 and to improve its lifespan after repeated washings, the fibre used to create the absorptive mat 10 may be a blend of the multi-limbed viscose rayon fibres discussed above together and a polyester fibre. It is possible to use between 5% and 40% polyester fibre with a preferred composition of 80% trilobal fibre and 20% polyester fibre. The addition of polyester fibres results in a reduction in the absorbency characteristics of the absorptive mat 10, but provides for increased strength, if required.

Referring particularly to FIGS. 5A and 5B, in application as a diaper 200, the present invention preferably includes an inner layer of a hydrophobic web of polyester fibres 220 and an impermeable pant-like garment 225 enveloping the reusable and absorptive mat 10 as hereinbefore described. The absorptive mat 10 thus forms a median layer 210 between an inner layer 220 of a hydrophobic web of polyester fibres, and an outer, impermeable pant-like garment layer 225. The inner layer 220 normally contacts the skin of the wearer, and is preferably constructed from a warp knitted tricot material stitched to give a desired porosity. The outer surface 215, possibly in contact with the skin of a parent, or caregiver, can be napped finished, for example by brushing to give a fibrous or padded texture that is comfortable next to the skin.

In application as an incontinence pad 100 as shown in FIG. 4, there is included an inner layer 120 of a hydrophobic web of polyester fibres, a median layer 110 constituted by an absorptive mat 10 as hereinbefore described and an impermeable outer layer 125.

To give a thick and comfortable appearance to the inner surface of the inner layer 120 or 220, it was found most desirable that the polyester fibre be knitted to a thickness of approximately 3 to 5 oz. per sq. yd., with a particularly preferable thickness being 4.4 oz. per sq. yd.

Referring now to FIGS. 4, 5A and 5B, the characteristics of the incontinence pad 100 or diaper 200 when in use are now described. When fluid waste from the wearer is discharged into the interior surface of the inner layer 120 or 220, the hydrophobic characteristic of the fibre prevents the fluid from collecting there. The fluid then seeps through the inner layer 120 or 220, down into the median layer 110 or 210 (that constitutes the absorptive mat 10), where it is absorbed, dispersed and retained. The dispersion characteristics of the median layer 110 or 210, that is the absorptive mat 10, of the present invention allows for quick and even dispersion in all directions towards various corners so that the viscose rayon fibres of the median layer 110 or 210 can retain a considerable amount of fluid without sogginess. In fact, the amount of fluid retained can approximate that of the inner absorptive layer of a disposable diaper or incontinence pad.

The outer, impermeable pant-like garment layer 225, or outer layer 125, provides further waterproofing, particularly for any outer clothing that might be worn over the diaper 200 or incontinence pad 100. The respective outer layer 125 or 225 is mounted to cover the bottom surface 105 or 205 of the viscose rayon median layer 110 or 210 and preferably includes a polyurethane film 130 or 245 that contacts the median layer 110 or 210, thereby preventing absorbed fluid from passing through the median layer 110 or 210. The outer layer 125 or 225 is preferably formed by means of a web of polyester fibre, which is preferably a warp knit tricot material stitched with a pre-stretched polyurethane film 130 or 245 bonded to the knitted polyester fibre. The pre-stretching gives the outer layer 125 or 225 a thick bumpy appearance, and provides additional strength. The thickness of the fibre portion of the outer layer 125 or 225 is normally between about 2.0 and 4.0 oz. per sq. yd., and preferably about 2.2 oz. per sq. yd.

The three layers 120, 110, 125 or 220, 210, 225 are preferably stacked together to form the incontinence pad 100 or diaper 200, respectively, and are preferably stitched together only around the periphery of their mated edges. Illustrated and described with reference to the diaper 200, and as shown in FIGS. 5A and 5B, a finishing edge 230 of woven polyester fibre is preferably sewn around the perimeter to give a smooth finish. The fluid receiving portion 235 of the median layer 210 is preferably unperforated by the stitching process. Alternatively, the inner layer 220 and the outer layer 225 can be so formed and stitched together, such that the median layer 210 is held in place with minimal or no stitching, for example by forming a pocket or envelope within which the median layer 210 is supported.

A diaper 200 according to the present invention can further include a mesh liner 240 which is removably placed onto the inner layer 220. The mesh liner 240 is used to collect solid excrement and can, together with the solid excrement, be flushed down the toilet for disposal in the sewage system. As such, the liner 240 is preferably made from a biodegradable fibrous mesh material. Alternatively, the liner 240 can be made from a polyester mesh material which can be washed and reused.

The diaper 200 of FIGS. 5a and 5b is preferably contoured in a substantially hourglass shape having a relatively narrow centre area 260 for fitting the diaper around the crotch (not shown) of the wearer. The diaper 200 is widened at its forward end to provide a pair of oppositely extending wing portions 250 for ease of folding and fastening around the trunk of the wearer. The narrow centre area 260 may also be gathered to provide a better fit around the leg of the wearer (not shown). A fastening means, such as buttons and buttonholes (not shown) may also be included to fasten the diaper around the wearer. Other modes of fastening the diaper such as pins, clips and various button types are also contemplated by the present invention.

Various other modifications and alterations may be used in the design and manufacture of the improved reusable diaper composition according to the present invention without departing from the spirit and scope of the invention, which is limited only by the accompanying claims. For example, the reusable and absorptive mat herein described can be adapted for various other applications or uses beyond the diaper or incontinence pad as disclosed. The inner and outer layers may be made of any suitable material and include various finishes or additives to provide desired characteristics. These may include odour masking additives, prints or other designs for aesthetic reasons, additional waterproofing layers, or additional layers for added comfort to the wearer. In addition, a plurality of reusable and absorptive mats or median layers as described may be combined to provide a greater degree of liquid absorption and retention.

The embodiments of the invention in which an exclusive property or privilege is claimed are defined as follows:

1. A reusable and washable absorptive mat for the absorption, dispersion and retention of a liquid comprising:
    a plurality of non-woven layers, of carded and randomly laid viscose rayon fibres having a cross-section of substantially rigid multi-limbed configuration,
    said layers stitchbonded in an as laid state, thereby substantially limiting entanglement and breaking of individual fibres, with a thread under limited tension so as to maintain uniformity of the absorptive mat.

2. A reusable and absorptive mat according to claim 1, wherein the viscose rayon fibres are of a trilobal configuration and have a water imbibition characteristic of from 100 to 345 percent.

3. A reusable and absorptive mat according to claim 2, wherein the layers are stitchbonded with a polyester thread in rows approximately 2 to 10 rows per inch, each of said rows having from 6 to 200 stitches per inch.

4. A reusable and absorptive mat according to claim 3, wherein said absorptive mat is pre-shrunk.

5. A washable and reusable pad for the absorption, dispersion and retention of liquids, said pad comprising:
    i. an interior layer of hydrophobic material including a receiving surface;
    ii. at least one median layer adjacent the interior layer opposite the receiving surface and comprising a plurality of non-woven layers, of carded and randomly laid viscose rayon fibres having a cross-section of substantially rigid multi-limbed configuration;
        said layers stitchbonded in an as laid state, thereby substantially limiting entanglement and breaking of individual fibres, with a thread under limited tension so as to maintain uniformity of the absorptive mat, and,
    iii. an outer layer of substantially waterproof polyurethane film adjacent the median layer.

6. A washable and reusable pad according to claim 5, wherein said interior layer, said at least one median layer, and said outer layer are joined only along outer edges thereof.

7. A washable and reusable pad according to claim 5, wherein said interior layer and said outer layer are joined to form an interior pocket for holding said at least one median layer.

8. A washable and reusable pad according to claim 5, wherein said viscose rayon fibres include recycled viscose rayon fibres.

9. A washable and reusable pad according to claim 8, wherein said viscose rayon fibres are blended with between 5% and 40% polyester fibres.

10. A washable and reusable pad according to claim 5, wherein said viscose rayon fibres are of trilobal configuration and have a water imbibition characteristic of from 100 to 345%.

11. A washable and reusable pad according to claim 5, wherein said median layer is preshrunk.

12. A washable and reusable pad according to claim 5, wherein said pad is contoured in an hourglass shape for wearing as a diaper and has a fastener device for securing said pad about a wearer.

13. A method for manufacturing a reusable and washable article for the absorption, dispersion and retention of a liquid comprising:
    i. providing a plurality of viscose rayon fibres having a cross-section of substantially rigid multi-limbed configuration;
    ii. carding said plurality of viscose rayon fibres,
    iii. randomly laying the carded plurality of viscose rayon fibres into a continuous random web structure to form a desired thickness; and,
    iv. stitchbonding said continuous random web structure in an as laid state, thereby limiting entanglement or breakage of individual fibres to form an absorptive mat.

14. A method of manufacturing a reusable and washable article according to claim 13, wherein said viscose rayon fibres are of a trilobal configuration and have a water imbibition characteristic of from 100 to 345 percent.

15. A method of manufacturing a reusable and washable article according to claim 14, wherein said stitchbonding step comprises stitchbonding with polyester thread in rows approximately 2 to 10 rows per inch, each of said rows having from 6 to 200 stitches per inch.

16. A method of manufacturing a reusable and washable article according to claim 13, further comprising:
    v. subjecting the stitchbonded mat to a heat treatment to reduce shrinkage when washed after use.

17. A method of manufacturing a reusable and washable article according to claim 16, wherein said heat treatment is at approximately 110° C.

18. A method of manufacturing a reusable and washable article according to claim 16 further comprising:
  vi. providing an interior layer of hydrophobic material having a receiving surface, said interior layer adjacent said absorptive mat opposite the receiving surface; and,
  vii. providing an outer layer of substantially waterproof polyurethane film adjacent said absorptive mat.

19. A method of manufacturing a reusable and washable article according to claim 18, further comprising:
  viii. adjoining said interior layer, said absorptive mat and said outer layer along the outer edges thereof to form a pad of unitary construction.

20. A method of manufacturing a reusable and washable article according to claim 18, further comprising:
  viii. adjoining said interior layer and said outer layer to form an envelope, said absorptive mat located within said envelope.

21. A method of manufacturing a reusable and washable article according to claim 20, wherein said article is contoured in an hourglass shape for wearing as a diaper and further providing a fastener for securing said diaper about a wearer.

* * * * *